United States Patent
Yamada et al.

(10) Patent No.: US 10,836,719 B2
(45) Date of Patent: Nov. 17, 2020

(54) PRODUCTION METHOD OF MALEIMIDE

(71) Applicant: UNITIKA LTD., Amagasaki (JP)

(72) Inventors: Yuki Yamada, Uji (JP); Tatsuya Morikita, Uji (JP); Yosuke Sugimoto, Uji (JP); Takeshi Yoshida, Uji (JP); Akira Shigeta, Uji (JP); Yoshiaki Echigo, Uji (JP)

(73) Assignee: UNITIKA LTD., Amagasaki (JP)

( * ) Notice: Subject to any disclaimer, the term of this patent is extended or adjusted under 35 U.S.C. 154(b) by 11 days.

(21) Appl. No.: 16/399,208

(22) Filed: Apr. 30, 2019

(65) Prior Publication Data

US 2019/0345102 A1 Nov. 14, 2019

(30) Foreign Application Priority Data

May 10, 2018 (JP) ................. 2018-091506

(51) Int. Cl.
| | | |
|---|---|---|
| C07D 207/448 | (2006.01) | |
| B01D 11/04 | (2006.01) | |
| B01D 9/00 | (2006.01) | |
| C07C 267/00 | (2006.01) | |

(52) U.S. Cl.
CPC ......... C07D 207/448 (2013.01); B01D 9/005 (2013.01); B01D 11/0492 (2013.01); C07C 267/00 (2013.01)

(58) Field of Classification Search
CPC ................................................. C07D 207/448
See application file for complete search history.

(56) References Cited

U.S. PATENT DOCUMENTS

| | | |
|---|---|---|
| H424 H | 2/1988 | Martin et al. |
| 5,973,166 A | 10/1999 | Mizori et al. |
| 6,281,314 B1 | 8/2001 | Tong et al. |
| 2004/0225026 A1 | 11/2004 | Mizori et al. |
| 2008/0262191 A1 | 10/2008 | Mizori |

FOREIGN PATENT DOCUMENTS

| | | |
|---|---|---|
| JP | 51-59851 A | 5/1976 |
| JP | 1-238568 A | 9/1989 |
| JP | 3-145462 A | 6/1991 |
| JP | 6-345730 A | 12/1994 |
| JP | 7-2768 A | 1/1995 |
| JP | 7-61969 A | 3/1995 |
| JP | 7-118230 A | 5/1995 |
| JP | 8-119939 A | 5/1996 |
| JP | 10-505599 A | 6/1998 |
| JP | 4198863 B2 | 12/2008 |
| JP | 4198908 B2 | 12/2008 |
| JP | 2012-117070 A | 6/2012 |
| WO | WO 96/07691 A2 | 3/1996 |

OTHER PUBLICATIONS

U.S. Appl. No. 15/872,463, filed Jan. 16, 2018.
U.S. Office Action dated May 28, 2020, for U.S. Appl. No. 16/555,675.
DeFusco et al., "A New Heat-Resistant Polymer From Dimer Diamine Bismaleimide," Naval Weapons Center, NWC TP 6543, AD-A145 664, Jul. 1984, pp. 1-24.
Japanese Decision of Refusal (including an English translation thereof) issued in the corresponding Japanese Patent Application No. 2018-004758 dated Jul. 31, 2018.
Japanese Notification of Reasons for Refusal (including an English translation thereof) issued in the corresponding Japanese Patent Application No. 2018-004758 dated Jun. 26, 2018.
Kita et al., "Mechanism of the Synthesis of N-Phenylmaleimide and Improvement of Its Selectivity," Bulletin of the Chemical Society of Japan, No. 4, 1996, pp. 375-384, with English abstract.
Sava, "Preparation and characterization of bismaleimide monomers with various structures," Designed Monomers and Polymers, vol. 16, No. 1, Jan. 2013, pp. 14-24.

*Primary Examiner* — Karen Cheng
(74) *Attorney, Agent, or Firm* — Birch, Stewart, Kolasch & Birch, LLP

(57) ABSTRACT

An object is to provide a method for easily producing maleimide (MI) in which trace amounts of residual acid components as impurities in a crude MI are efficiently reduced, that is, the acid value is sufficiently reduced.

<1> A method for producing purified MI, comprising reducing an acid value of crude MI by 50% or more, by adding carbodiimide (CDI) to a solution comprising the crude MI to react an acid component in the crude MI with the CDI.

<2> The method for producing purified MI, comprising adding 0.5% by mass or more and 8% by mass or less of the CDI with respect to a mass of the crude MI for reaction.

<3> The method for producing purified MI, wherein the CDI is N,N'-diisopropyl carbodiimide (DIC).

<4> The method for producing purified MI, comprising removing a urea derivative of the CDI (CDI-U) by-produced when reacting the acid component in the crude MI with the CDI.

8 Claims, No Drawings

PRODUCTION METHOD OF MALEIMIDE

ART FIELD RELATED

The present invention relates to a method for producing maleimide (hereinafter sometimes abbreviated as "MI") useful as a laminating material, a sealing material, an electrical insulating material, a conductive paste, an adhesive, a pressure-sensitive adhesive, a structural material, or the like.

PRIOR ART

MI is produced by, for example, reacting an amine with maleic anhydride in a solvent in the presence of an acid catalyst to form a maleamic acid (hereinafter sometimes abbreviated as "MAA"), and then maleimidizing (ring-closing by dehydration) the MAA with an acid catalyst or the like to prepare a crude MI solution, followed by purification. MI is widely used as a laminating material, a sealing material, an electrical insulating material, a conductive paste, an adhesive, a pressure-sensitive adhesive, a structural material and the like. In the produced MI, trace amounts of acid components such as MAA, fumaramic acid, Michael adduct and the like remain as impurities. When used as an adhesive or a pressure-sensitive adhesive for a semiconductor, these acid components may be responsible for corrosion caused by MI in a semiconductor device. In addition, the acid components in MI may cause deterioration of dielectric property, electrical insulation and the like. Furthermore, the acid components in MI may cause reduction of heat resistance and increase of weight loss ratio at high temperature. Accordingly, various methods have been proposed for reducing trace amounts of residual acid components in the MI purification process, that is, for reducing the acid value of MI. For example, Patent Documents 1 to 9 disclose methods for reducing acid components by, prior to the purification, repeatedly purifying a crude MI solution by methods such as reprecipitation, water washing and crystallization. Note that, Non-Patent Document 1 discloses that a crude MI solution obtained by reacting an amine with maleic anhydride to form a maleamic acid, and then maleimidizing the maleamic acid with an acid catalyst or the like contains acid components as described above.

PRIOR ART DOCUMENTS

[Patent Documents]
[Patent Document 1] JP 01-238568 A
[Patent Document 2] JP 03-145462 A
[Patent Document 3] JP 06-345730 A
[Patent Document 4] JP 07-002768 A
[Patent Document 5] JP 07-061969 A
[Patent Document 6] JP 07-118230 A
[Patent Document 7] JP 08-119939 A
[Patent Document 8] JP 4198863 B2
[Patent Document 9] JP 4198908 B2
[Non-Patent Document]
[Non-Patent Document 1] Journal of the Chemical Society of Japan, 1996, (4), pages 375-384

DISCLOSURE OF INVENTION

Technical Problems to be Solved

However, in the publicly known methods including repeating reprecipitation, water washing, crystallization and the like, the acid component-reducing effect is not sufficient, and the process is complicated.

Accordingly, an object of the present invention is to provide a method for easily producing purified MI in which trace amounts of residual acid components as impurities in a crude MI have been efficiently reduced, that is, the acid value has been sufficiently reduced.

Means to Solve the Problems

It has been found that the acid value of crude MI is significantly reduced by reacting trace amounts of residual acid components in the crude MI with a specific compound, and the present invention has been accomplished.

The present invention is as follows.

<1> A method for producing purified MI, comprising reducing an acid value of crude MI by 50% or more, by adding carbodiimide (CDI) to a solution comprising the crude MI to react the acid component in the crude MI with the CDI.

<2> The method for producing purified MI, comprising adding 0.5% by mass or more and 8% by mass or less of the CDI with respect to a mass of the crude MI for reaction.

<3> The method for producing purified MI, wherein the CDI is N,N'-diisopropyl carbodiimide (DIC).

<4> The method for producing purified MI, comprising removing a urea derivative of the CDI (CDI-U) by-produced when reacting the acid component in the crude MI with the CDI.

<5> The method for producing purified MI, wherein a method for removing the CDI-U is a reprecipitation method or a solvent extraction method.

<6> The method for producing purified MI, wherein a solvent used for the reprecipitation method or the solvent extraction method is methanol.

Effects of the Invention

The purified MI obtained by the production method of the present invention is excellent in corrosion resistance, dielectric property, electrical insulation and heat resistance, because acid components are sufficiently reduced. Therefore, the purified MI can be suitably used as a component of an adhesive, a pressure-sensitive adhesive or a sealant applied to a semiconductor or the like.

MODE FOR CARRYING OUT THE INVENTION

Hereinafter, a detailed description is made of the present invention.

MI used in the production method of the present invention uses as an amine component composing the MI a monoamine and/or polyamine (diamine, triamine etc.) of aliphatic amines, alicyclic amines or aromatic amines (including heterocyclic amines).

Specific examples of the aliphatic amines may include methylamine, ethylamine, n-propylamine, iso-propylamine, n-butylamine, n-pentylamine, n-hexylamine, n-octylamine, decylamine, 1,2-ethylenediamine, 1,2-diaminopropane, 1,3-diaminopropane, 1,4-diaminobutane, 1,5-diaminopentane, 1,6-diaminohexane, 2-methyl-1,5-diaminopentane, 1,7-diaminoheptane, 1,8-diaminooctane, 1,9-diaminononane, 1,10-diaminodecane, 1,11-diaminoundecane, 1,12-diaminododecane, dimer diamine (hereinafter sometimes abbreviated as "DDA") and the like.

These may be used alone or in combination of two or more. Among them, DDA is preferable. DDA is an aliphatic amine derived from a dimeric acid having 24 to 48 carbon atoms. DDA is obtained by, for example, polymerizing an unsaturated fatty acid such as oleic acid or linoleic acid to form a dimeric acid, followed by reduction and amination (reductive amination). As DDA, a commercially available product such as "Priamine 1074, 1075" (trade name, made by Croda Japan KK) or "Versamine 551, 552" (trade name, made by Cognis Japan Ltd.) may be used.

As the aliphatic amines, "imide-extended amines" as described in US 2008/0,262,191 A, JP 2012-117070 A may also be preferably used. Here, the imide-extended amines are "polyimides or oligoimides having amino groups at both ends" obtained by reacting tetracarboxylic dianhydride with an excess amount of aliphatic amine, followed by dehydration for ring-closure. Specific examples of the tetracarboxylic dianhydride may include pyromellitic dianhydride (PMDA), 3,3',4,4'-biphenyltetracarboxylic dianhydride, 2,3,3',4'-biphenyltetracarboxylic dianhydride, 3,3',4,4'-benzophenonetetracarboxylic dianhydride (BTDA), 4,4'-oxydiphthalic anhydride (ODPA), 2,2-bis(3,4-dicarboxyphenyl) propane dianhydride (BDCP), 3,3',4,4'-diphenylsulfonetetracarboxylic dianhydride and the like. These may be used alone or in combination of two or more. Among them, PMDA, ODPA or BDCP is preferable. In addition, as an aliphatic amine composing the "imide-extended amine", the above-described aliphatic amines may be used, and DDA is preferable.

Specific examples of the alicyclic amines may include cyclohexylamine, 1,3-bis(aminomethyl)cyclohexane, 1,4-bis(aminomethyl)cyclohexane, 1,4-diaminocyclohexane, 4,4'-methylenebis(cyclohexylamine), 4,4'-methylenebis(2-methylcyclohexylamine), 3,9-bis(3-aminopropyl)-2,4,8,10-tetraoxaspiro[5.5]-undecane and the like.

Specific examples of the aromatic amines may include aniline, toluidine, naphthylamine, 2,2'-bis[4-(4-aminophenoxy)phenyl]propane (BAPP), 4,4'-diaminodiphenylmethane (MDA), m-phenylenediamine (MPD), 4,4'-diaminodiphenyl ether, 2'-methoxy-4,4'-diaminobenzanilide, 1,4-bis (4-aminophenoxy)benzene, 1,3-bis(4-aminophenoxy) benzene, 2,2'-bis[4-(4-aminophenoxy)phenyl]propane (BAPP), 2,2'-dimethyl-4,4'-diaminobiphenyl, 3,3'-dihydroxy-4,4'-diaminobiphenyl, 4,4'-diaminobenzanilide, bisaniline fluorene, 2,2-bis-[4-(3-aminophenoxy)phenyl]propane, bis[4-(4-aminophenoxy)phenyl]sulfone, bis[4-(3-aminophenoxy)phenyl]sulfone, bis[4-(4-aminophenoxy)] biphenyl, bis[4-(3-aminophenoxy)biphenyl, bis[1-(4-aminophenoxy)]biphenyl, bis[1-(3-aminophenoxy)] biphenyl, bis[4-(4-aminophenoxy)phenyl]methane, bis[4-(3-aminophenoxy)phenyl]methane, bis[4-(4-aminophenoxy)phenyl]ether, bis[4-(3-aminophenoxy) phenyl]ether, bis[4-(4-aminophenoxy)]benzophenone, bis [4-(3-aminophenoxy)]benzophenone, bis[4,4'-(4-aminophenoxy)]benzanilide, bis[4,4'-(3-aminophenoxy)] benzanilide, 9,9-bis[4-(4-aminophenoxy)phenyl]fluorene, 9,9-bis[4-(3-aminophenoxy)phenyl]fluorene, 2,2-bis-[4-(4-aminophenoxy)phenyl]hexafluoropropane, 2,2-bis-[4-(3-aminophenoxy)phenyl]hexafluoropropane, 4,4'-methylene di-o-toluidine, 4,4'-methylene di-2,6-xylidine, 4,4'-methylene-2,6-diethylaniline, 4,4'-diaminodiphenylpropane, 3,3'-diaminodiphenylpropane, 4,4'-diaminodiphenylethane, 3,3'-diaminodiphenylethane, 3,3'-diaminodiphenylmethane, 4,4'-diaminodiphenyl sulfide, 3,3'-diaminodiphenyl sulfide, 4,4'-diaminodiphenyl sulfone, 3,3'-diaminodiphenyl sulfone, 3,3-diaminodiphenyl ether, 3,4'-diaminodiphenyl ether, benzidine, 3,3'-diaminobiphenyl, 3,3'-dimethyl-4,4'-diaminobiphenyl, 3,3'-dimethoxybenzidine, 4,4"-diamino-p-terphenyl, 3,3"-diamino-p-terphenyl, p-phenyleneamine, 2,6-diaminopyridine, 1,4-bis (4-aminophenoxy)benzene, 1,3-bis (4-aminophenoxy)benzene, 4,4'-[1,4-phenylenebis(1-methylethylidene)]bisaniline, 4,4'-[1,3-phenylenebis(1-methylethylidene)]bisaniline, bis(p-aminocyclohexyl) methane, bis(p-β-amino-t-butylphenyl)ether, bis(p-β-methyl-δ-aminopentyl)benzene, p-bis(2-methyl-4-aminopentyl)benzene, p-bis (1,1-dimethyl-5-aminopentyl) benzene, 1,5-diaminonaphthalene, 2,6-diaminonaphthalene, 2,4-bis(β-amino-t-butyl)toluene, 2,4-diaminotoluene, m-xylene-2,5-diamine, p-xylene-2,5-diamine, m-xylylenediamine, p-xylylenediamine, 2,6-diaminopyridine, 2,5-diaminopyridine, 2,5-diamino-1,3,4-oxadiazole and the like. These may be used alone or in combination of two or more. Among them, MDA, MPD or BAPP is preferable.

A crude MI solution used in the production method of the present invention can be obtained using a publicly known method. That is, the crude MI solution can be obtained by, for example, reacting the above-described amine with a substantially equivalent amount of maleic anhydride in a solvent at a temperature of 0° C. to 50° C. to form a MAA, and then dehydrating for ring-closure (maleimidization) the MAA at a temperature of 50° C. to 200° C. in the presence of an acid catalyst. The solvent for use is not limited, but is preferably a hydrocarbon solvent such as toluene, xylene (o-xylene, m-xylene, p-xylene), ethylbenzene or mesitylene, an amide solvent such as N,N-dimethylformamide, N,N-dimethylacetamide or N-methyl-2-pyrrolidone (NMP), a mixed solvent of the hydrocarbon solvent and the amide solvent, or the like.

In addition, there is no limitation on the acid catalyst for use, but sulfuric acid, formic acid, methanesulfonic acid, benzenesulfonic acid, orthophosphoric acid, metaphosphoric acid, pyrophosphoric acid, phosphorous acid, hypophosphorous acid, maleic acid, a cationic ion exchange resin and the like may be used. Triethylamine salts of these acids may also be used. When performing the dehydration for ring-closure, it is preferable to remove water generated by the maleimidization to the outside of the reaction system by azeotropy or the like.

In the MI production method of the present invention, acid components are reduced from the crude MI solution obtained as described above to reduce the acid value of the crude MI by reacting trace amounts of residual acid components as impurities in the crude MI with CDI. The acid value reduction rate needs to be 50% or more, preferably 70% or more, more preferably 90% or more. Here, the acid value reduction rate refers to a value calculated using the following equation.

Acid value reduction rate (%)=100×(acid value of crude MI–acid value of purified MI)/acid value of crude MI In the production method of the present invention, there is no limitation on the acid value of the crude MI, but it is preferable to use a crude MI having an acid value of 30 mg-KOH/g or less.

When acid components in the crude MI are reacted with CDI, a maleimide generated by the dehydration for ring-closure of the acid component, and a urea derivative of the CDI (CDI-U) are both produced as main products. The MI solution containing the CDI-U after the reaction can be used as an MI, not only when the CDI-U is removed to reduce the acid value, but also as it is.

As the crude MI, commercially available MIs can be used. Because the commercial products have a trace amount of residual acid component, it is desired that the acid value be reduced.

As the CDI, monocarbodiimides, polycarbodiimides, cyclic carbodiimides and the like may be used. Specific examples of the monocarbodiimides may include bis(2,6-diisopropylphenyl)carbodiimide, diphenyl carbodiimide, di-β-naphthyl carbodiimide, N,N'-diisopropyl carbodiimide (DIC), 1-ethyl-3-(3-dimethylaminopropyl)carbodiimide (EDC), dimethyl carbodiimide, diisobutyl carbodiimide, dioctyl carbodiimide, t-butyl isopropyl carbodiimide, di-t-butylcarbodiimide, N,N'-dicyclohexylcarbodiimide (DCC) and the like. Specific examples of the polycarbodiimides (the number average molecular weight: 300-20000) may include poly(1,6-hexamethylene carbodiimide), poly(4,4'-methylenebiscyclohexyl carbodiimide), poly(1,3-cyclohexylene carbodiimide), poly(1,4-cyclohexylene carbodiimide), poly(4,4'-dicyclohexylmethane carbodiimide), poly(4,4'-diphenylmethanecarbodiimide), poly(3,3'-dimethyl-4,4'-diphenylmethanecarbodiimide), poly(naphthylene carbodiimide), poly(p-phenylene carbodiimide), poly(m-phenylene carbodiimide), poly(tolylcarbodiimide), poly(methyl-diisopropyl phenylene carbodiimide), poly(1,3,5-triisopropylbenzene carbodiimide), poly(1,3,5-triisopropylbenzene and 1,5-diisopropylbenzene carbodiimide), poly(triethyl phenylene carbodiimide), poly(triisopropyl phenylene carbodiimide), poly(diisopropyl carbodiimide) and the like. These may be used alone or in combination of two or more. Among the carbodiimides, preferable are monocarbodiimides making it easy to remove carbodiimide derivatives such as a CDI-U produced as a by-product after the reaction. Among the monocarbodiimides, DIC or EDC is more preferable, and DIC is particularly preferable. As the polycarbodiimides, commercially available products such as "Carbodilite" (trade name, made by Nisshinbo Chemical Inc.) and "Stabaxol" (trade name, made by Rhein Chemie) may be used. In addition, as the cyclic carbodiimides, "TCC" (trade name, made by Teijin Limited) may be used.

In order to react trace amounts of residual acid components in the crude MI with the CDI, it is preferable to add 0.5% by mass or more and 8% by mass or less of CDI with respect to the mass of crude MI for the reaction in a solvent. The lower limit of the added amount of CDI is more preferably 1% by mass or more, still more preferably 2% by mass or more. The upper limit of the added amount of CDI is more preferably 7% by mass or less, still more preferably 6% by mass or less. Note that, when the added amount of CDI is less than the above-described lower limit, it may be impossible to reduce the acid value of crude MI by 50% or more. In addition, when the added amount of CDI exceeds the above-described upper limit, unreacted CDI may remain in a purified MI.

The reaction temperature in the reaction is preferably 40 to 150° C., more preferably 60 to 120° C. The reaction time in the reaction is preferably 0.5 to 10 hours, more preferably 1 to 8 hours. The concentration of MI in the reaction is preferably 20 to 70% by mass. The reaction solvent is not limited, but is preferably a hydrocarbon solvent such as toluene, xylene, heptane or octane, an amide solvent such as N,N-dimethylformamide, N, N-dimethylacetamide or N-methyl-2-pyrrolidone (NMP) or the like. In this way, the acid value of MI can be efficiently reduced by reacting acid components in the crude MI with the CDI.

In this reaction, although when the CDI reacts with acid components in the crude MI, CDI-Us are by-produced, as described above, they can be removed from the MI solution after the reaction. That is, the purified MI can be separated from the CDI-Us by methods such as a method for recovering the purified MI by reprecipitation of MI from the MI solution and a method for removing the CDI-Us from the MI solution by solvent extraction or filtration. Among these CDI-U removal methods, it is preferable to use a reprecipitation method or a solvent extraction method. As a precipitating agent in the reprecipitation method and a solvent in the solvent extraction method, water, methanol, ethanol, acetone or a mixture thereof may be used, and methanol is preferable. Because urea derivatives of the above-described DIC and EDC are soluble in these solvents, they can be easily removed from the reaction solution by reprecipitation or solvent extraction.

The removed CDI-U can be regenerated to CDI by performing a publicly known method, for example, a dehydration reaction using a dehydration catalyst etc., and the regenerated CDI may be repeatedly used.

When the CDI reacts with acid components in the crude MI, in addition to the CDI-U that is the main product, O-acylisourea or N-acylurea may be formed, which is an acylurea derivative of acid components remaining in the crude MI. The acid value of MI is also reduced by the formation of this acylurea derivative.

Note that, when the crude MI is used in which the above-described "imide-extended amine" is used and the polycarbodiimide is used as the CDI, acid components in the crude MI are further chain-extended via the acyl urea bond.

As to the formation of acylurea derivative by reaction of the CDI with acid components, reference can be made to Tetrahedron 63 (28) 6508-6511 (2007) etc.

As described above, because the MI obtained by the production method of the present invention has a significantly reduced acid value, the MI can be suitably used as a component for adhesives or a pressure-sensitive adhesive for use in production of semiconductor. When applying the MI in such a field, reference can be made to patent documents such as WO 2016/167245, JP 6005313 B2, JP 6005313 B2, JP 6005312 B2, JP 5989928 B2, JP 5972490 B2 and JP 5972489 B2. Note that, for example, JP 6005313 B2 discloses that MI has "a weight loss ratio of less than 1% when heated at 250° C. for 2 hours in a nitrogen atmosphere", and thus it is preferable that when using MI in such a field, the weight loss ratio be low at high temperature. Because the MI obtained by the production method of the present invention has a significantly reduced acid value, the weight loss due to acid components remaining in the MI is significantly reduced. Accordingly, the MI is excellent in heat resistance.

EXAMPLES

Hereinafter, a detailed description is made of Examples of the present invention, but the present invention is not limited only to the Examples.

Example 1

As a crude MI solution, a toluene solution (the concentration: 50% by mass) of BMI-3000 which was commercially available from Designer Molecules Inc. (hereinafter sometimes abbreviated as "DMI") was prepared. This MI is an MI which uses DDA that is imide-extended with PMDA as the amine component. The acid value was 5.63 mg-KOH/g. To 100 g of this crude MI solution, 1.2 g of DIC was added for reaction at 90° C. for 5 hours. After cooling, a solution obtained by adding toluene to this reaction solution was added to a large amount of methanol under stirring to reprecipitate the MI, and by-produced urea derivatives of the DIC were dissolved in methanol for removal. Subsequently, the precipitate was mixed with toluene to prepare a purified MI solution having an MI concentration of 50% by mass. By measuring the acid value of this solution, the acid value reduction rate was calculated. The results are shown in Table 1. Note that, the acid value is a value measured by the neutralization titration method based on the standard of JIS K 0070 (1992).

Example 2

To 100 g of the crude MI solution used in Example 1, 1.8 g of DIC was added for reaction at 70° C. for 5 hours. After cooling, a solution obtained by adding toluene to this reaction solution was subjected to solvent extraction using a mixed solvent of methanol and water to remove urea derivatives of the DIC. The obtained solution in toluene was concentrated to prepare a purified MI solution having an MI concentration of 50% by mass, and the acid value reduction rate was calculated. The results are shown in Table 1.

Example 3

As a crude MI solution, a toluene solution (the concentration: 50% by mass) of BMI-1500 which was commercially available from DMI was prepared. This MI is an MI which uses DDA that is imide-extended with ODPA as the amine component. Using this MI, in the same manner as in Example 1, a purified MI solution was obtained, and the acid value reduction rate was calculated. The results are shown in Table 1.

Example 4

As a crude MI solution, a toluene solution (the concentration: 50% by mass) of BMI-689 which was commercially available from DMI was prepared. This MI is an MI which uses DDA as the amine component. To 100 g of this crude MI solution, 1.2 g of DIC was added for reaction at 60° C. for 5 hours. After cooling, a purified MI solution without removal of urea derivatives of the DIC from this reaction solution was prepared having an MI concentration of 50% by mass by dilution with toluene, and the acid value reduction rate was calculated. The results are shown in Table 1.

Example 5

As a crude MI solution, a toluene solution (the concentration: 50% by mass) of BMI-1700 which was commercially available from DMI was prepared. This MI is an MI which uses DDA that is imide-extended with BDCP as the amine component. Using this MI, in the same manner as in Example 1, a purified MI solution was obtained, and the acid value reduction rate was calculated. The results are shown in Table 1.

Example 6

In the same manner as in Example 1 except that EDC was used as CDI, a purified MI solution was obtained, and the acid value reduction rate was calculated. The results are shown in Table 1.

Example 7

As a crude MI solution, a NMP solution (the concentration: 30% by mass) of B-1109 which was commercially available from Tokyo Chemical Industry was prepared. This MI is an MI which uses MDA as the amine component. To 100 g of this crude MI solution, 0.8 g of DIC was added for reaction at 90° C. for 5 hours. After cooling, the reaction solution was added to a large amount of methanol under stirring to reprecipitate the MI. The reprecipitated MT was filtered off, washed with methanol and then dried to prepare a purified MI powder. By measuring the acid value, the acid value reduction rate was calculated. The results are shown in Table 1.

Example 8

As a crude MI solution, a NMP solution (the concentration: 30% by mass) of B-4807 which was commercially available from Tokyo Chemical Industry was prepared. This MI is an MI which uses BAPP as the amine component. Using this MI, in the same manner as in Example 7, a purified MI powder was obtained, and the acid value reduction rate was calculated. The results are shown in Table 1.

Example 9

As a crude MI solution, a NMP solution (the concentration: 30% by mass) of P-0976 which was commercially available from Tokyo Chemical Industry was prepared. This MI is an MI which uses MPD as the amine component. Using this MI, in the same manner as in Example 7, a purified MI powder was obtained, and the acid value reduction rate was calculated. The results are shown in Table 1.

Example 10

In the same manner as in Example 7 except that the added amount of DIC was 1.8 g, a purified MI powder was obtained, and the acid value reduction rate was calculated. The results are shown in Table 1.

Example 11

In the same manner as in Example 7 except that the added amount of DIC was 0.50 g, a purified MI powder was obtained, and the acid value reduction rate was calculated. The results are shown in Table 1.

Example 12

In the same manner as in Example 7 except that the added amount of DIC was 0.20 g, a purified MI powder was obtained, and the acid value reduction rate was calculated. The results are shown in Table 1.

Example 13

To 100 g of a solution of B-1109 in NMP (the concentration: 30% by mass) used in Example 7 was added 1.2 g of polycarbodiimide (Carbodilite V-05 made by Nisshinbo Chemical Inc.) to prepare an MI solution. Then, this MI solution was reacted at 90° C. for 5 hours to prepare a purified BMI solution, and the acid value reduction rate was calculated. The results are shown in Table 1.

Example 14

To 100 g of a solution of B-1109 in NMP (the concentration: 30% by mass) used in Example 7 was added 1.8 g of polycarbodiimide (Carbodilite V-05 made by Nisshinbo Chemical Inc.) to prepare an MI solution. Then, this MI solution was reacted at 90° C. for 5 hours to prepare a purified BMI solution, and the acid value reduction rate was calculated. The results are shown in Table 1.

Example 15

In the same manner as in Example 13 except that polycarbodiimide (Stabaxol P (the molecular weight: 3,000-4,000, made by Rhein Chemie)) was used as CDI, a purified MI solution was obtained, and the acid value reduction rate was calculated. The results are shown in Table 1.

Example 16

To 100 g of a solution of BMI-3000 in toluene (the concentration: 50% by mass) used in Example 1 was added 1.2 g of polycarbodiimide (Carbodilite V-05 made by Nisshinbo Chemical Inc.) to prepare an MI solution. Then, this MI solution was reacted at 90° C. for 5 hours to prepare a purified BMI solution, and the acid value reduction rate was calculated. The results are shown in Table 1.

Example 17

In the same manner as in Example 7 except that the added amount of DIC was 0.63 g, a purified MI powder was obtained, and the acid value reduction rate was calculated. The results are shown in Table 1.

Example 18

A solution of the powder obtained in Example 17 in NMP (the concentration: 30% by mass) was prepared. To 100 g of this crude MI solution, 0.33 g of DIC was added for reaction at 70° C. for 5 hours. After cooling, the reaction solution was added to a large amount of methanol under stirring to reprecipitate the MI. The reprecipitated MI was filtered off, washed with methanol and then dried to prepare a purified MI powder. By measuring the acid value, the acid value reduction rate was calculated. The results are shown in Table 1.

Comparative Example 1

As a crude MI solution, the solution of BMI-3000 in toluene used in Example 1 was used. Operation of adding to the solution an equal amount of water, followed by stirring, and then separating the toluene phase from the aqueous phase was performed three times to prepare a water-washed MI solution, and the acid value reduction rate was calculated. The results are shown in Table 1.

Comparative Example 2

As a crude MI solution, the solution of BMI-3000 in toluene used in Example 1 was used. Operation of adding to the solution an equal amount of 2% ammonium solution, followed by stirring, and then separating the toluene phase from the aqueous phase was performed three times, followed by water-washing, to prepare a ammonium solution-washed MI solution, and the acid value reduction rate was calculated. The results are shown in Table 1.

Comparative Example 3

As a crude MI solution, the solution of B-1109 in NMP used in Example 7 (the concentration: 30% by mass) was prepared. After cooling, operation in which the reaction solution was added to a large amount of methanol under stirring to reprecipitate the MI, and the reprecipitated MI was filtered off, washed with methanol and then dried was repeated three times. By measuring the acid value, the acid value reduction rate was calculated. The results are shown in Table 1.

Comparative Example 4

In the same manner as in Example 7 except that the added amount of DIC was 0.13 g, an MI powder was obtained, and the acid value reduction rate was calculated. The results are shown in Table 1.

Comparative Example 5

In the same manner as in Example 7 except that the added amount of DIC was 0.10 g, an MI powder was obtained, and the acid value reduction rate was calculated. The results are shown in Table 1.

Comparative Example 6

In the same manner as in Example 13 except that the added amount of polycarbodiimide (Carbodilite V-05 made by Nisshinbo Chemical Inc.) was 0.13 g, an MI solution was obtained, and the acid value reduction rate was calculated. The results are shown in Table 1.

Comparative Example 7

In the same manner as in Example 13 except that the added amount of polycarbodiimide (Carbodilite V-05 made by Nisshinbo Chemical Inc.) was 0.10 g, an MI solution was obtained, and the acid value reduction rate was calculated. The results are shown in Table 1.

TABLE 1

| | ADDED AMOUNT OF CDI (%) | ACID VALUE (mg-KOH/g) | | ACID VALUE REDUCTION RATE (%) |
|---|---|---|---|---|
| | | CRUDE MI | PURIFIED MI | |
| EXAMPLE 1 | 2.4 | 5.63 | 0.31 | 94.5 |
| EXAMPLE 2 | 3.6 | 5.63 | 0.16 | 97.2 |
| EXAMPLE 3 | 2.4 | 6.44 | 0.37 | 94.3 |
| EXAMPLE 4 | 2.4 | 3.12 | 0.18 | 94.2 |
| EXAMPLE 5 | 2.4 | 5.01 | 0.29 | 94.2 |
| EXAMPLE 6 | 2.4 | 5.63 | 0.21 | 96.3 |
| EXAMPLE 7 | 2.7 | 11.09 | 0.39 | 96.5 |
| EXAMPLE 8 | 2.7 | 6.44 | 0.31 | 95.2 |
| EXAMPLE 9 | 2.7 | 3.23 | 0.18 | 94.4 |
| EXAMPLE 10 | 6.0 | 11.09 | 0.29 | 97.4 |
| EXAMPLE 11 | 1.7 | 11.09 | 2.41 | 78.3 |
| EXAMPLE 12 | 0.6 | 11.09 | 5.28 | 52.4 |
| EXAMPLE 13 | 4.0 | 11.09 | 1.52 | 86.3 |
| EXAMPLE 14 | 6.0 | 11.09 | 0.89 | 92.0 |
| EXAMPLE 15 | 4.0 | 11.09 | 2.36 | 78.7 |
| EXAMPLE 16 | 2.4 | 5.63 | 1.25 | 77.8 |
| EXAMPLE 17 | 2.1 | 11.09 | 1.72 | 84.5 |
| EXAMPLE 18 | 1.1 | 1.72 | 0.10 | 94.2 |
| COMPARATIVE EXAMPLE 1 | — | 5.63 | 5.61 | 0.4 |
| COMPARATIVE EXAMPLE 2 | — | 5.63 | 5.57 | 1.1 |
| COMPARATIVE EXAMPLE 3 | — | 11.09 | 10.86 | 2.1 |
| COMPARATIVE EXAMPLE 4 | 0.4 | 11.09 | 6.92 | 37.6 |
| COMPARATIVE EXAMPLE 5 | 0.3 | 11.09 | 9.41 | 15.1 |

TABLE 1-continued

| | ADDED AMOUNT OF CDI (%) | ACID VALUE (mg-KOH/g) CRUDE MI | ACID VALUE (mg-KOH/g) PURIFIED MI | ACID VALUE REDUCTION RATE (%) |
|---|---|---|---|---|
| COMPARATIVE EXAMPLE 6 | 0.4 | 11.09 | 9.89 | 10.8 |
| COMPARATIVE EXAMPLE 7 | 0.3 | 11.09 | 10.45 | 5.8 |

Added amount of CDI (%)=100×mass of CDI/mass of crude CDI

As shown in the Examples and Comparative Examples, it is understood that the acid value of the MI obtained by the production method of the present invention is efficiently reduced.

INDUSTRIAL APPLICABILITY

According to the production method of the present invention, an MI having a reduced acid value can be efficiently obtained. Because the obtained MI has a reduced acid value, the MI is excellent in corrosion resistance, electrical property and heat resistance. Accordingly, the MI is useful as a laminating material, a sealing material, an electrical insulating material, a conductive paste, an adhesive, a pressure-sensitive adhesive, a structural material and the like.

The invention claimed is:

1. A method for producing purified maleimide (MI), comprising reducing an acid value of crude MI by 50% or more, by adding carbodiimide (CDI) to a solution comprising the crude MI containing an acid component to react the acid component in the crude MI with the CDI.

2. The method for producing purified MI of claim 1, comprising adding 0.5% by mass or more and 8% by mass or less of the CDI with respect to a mass of the crude MI for reaction.

3. The method for producing purified MI of claim 1, wherein the CDI is N,N'-diisopropyl carbodiimide (DIC).

4. The method for producing purified MI of claim 1, comprising removing a urea derivative of the CDI (CDI-U) by-produced when reacting the acid component in the crude MI with the CDI.

5. The method for producing purified MI of claim 4, wherein a method for removing the CDI-U is a reprecipitation method or a solvent extraction method.

6. The method for producing purified MI of claim 5, wherein a solvent used for the reprecipitation method or the solvent extraction method is methanol.

7. The method for producing purified MI of claim 2, wherein the CDI is N,N'-diisopropyl carbodiimide (DIC).

8. The method for producing purified MI of claim 2, comprising removing a urea derivative of the CDI (CDI-U) by-produced when reacting the acid component in the crude MI with the CDI.

* * * * *